United States Patent [19]
Hippensteel

[11] Patent Number: 5,934,297
[45] Date of Patent: Aug. 10, 1999

[54] DENTAL FLOSS HOLDER WITH AN AUTOMATIC FLOSS TENSIONING MEANS

[76] Inventor: Joseph B. Hippensteel, 1596 Belle Isle Cir., NE. Atlanta, Ga. 30329

[21] Appl. No.: 09/232,944

[22] Filed: Jan. 19, 1999

Related U.S. Application Data

[63] Continuation of application No. 08/853,137, May 8, 1997, Pat. No. 5,860,435.
[51] Int. Cl.$^6$ .................................................. A61C 15/00
[52] U.S. Cl. .......................................... 132/327; 132/326
[58] Field of Search .................................. 132/323, 324, 132/325, 326, 327

[56] References Cited

U.S. PATENT DOCUMENTS

| | | | |
|---|---|---|---|
| D. 251,075 | 2/1979 | Schiff | 132/323 |
| 2,217,917 | 10/1940 | Munro | 132/326 |
| 5,538,023 | 7/1996 | Oczkowski et al. | 132/323 |

*Primary Examiner*—Todd E. Manahan
*Attorney, Agent, or Firm*—Caesar, Rivise, Bernstein, Cohen & Pokotilow, Ltd.

[57] ABSTRACT

A dental flossing holder adapted to be held by a hand of a user for holding and manipulating a length of dental floss. The holder comprises a housing having an opening for dispensing a desired length of dental floss and a storage compartment located within the housing for storing dental floss to be dispensed. A tensioning means extends from the housing and comprises a pair of opposed support members each member having a free end. An anchoring means is located at the free end of each support member. The anchoring means is provided for removably anchoring the length of dental floss between the free ends of the support members. The support members are moveable with respect to each other from a first position defined by a first distance between the free ends to a second position defined by a second distance between the free ends, the second distance being greater than the first distance. An actuating means is coupled to the tensioning means and is operable in response to the user biting thereon to cause the support members to move from the first position to the second position to exert tension on the floss and enable the abrasion and removal of plaque and food particles from interproximal surfaces of teeth.

18 Claims, 5 Drawing Sheets

DENTAL FLOSS HOLDER WITH AN AUTOMATIC FLOSS TENSIONING MEANS

RELATED APPLICATIONS

This application is a continuation of U.S. patent application Ser. No. 08/853,137 filed on May 8, 1997 now U.S. Pat. No. 5,860,435.

BACKGROUND OF THE INVENTION

The benefits of using dental floss for removal of plaque from teeth have been known for many years. Daily flossing is recommended by almost all dentists. Nevertheless, because of the difficulty, inconvenience and messiness involved in manipulating the floss and the time of several minutes that is required, very few people actually use dental floss on a daily basis.

The use of dental floss is a difficult task at best. It is very awkward, messy and cumbersome to hold a length of dental floss on the ends of fingers in one's own mouth. The space limitations are such that reciprocal movement with the fingers is nearly impossible. It is also very difficult to move the dental floss up and down to scrape the sides of the teeth. Moreover, applying dental floss using one's fingers is very wasteful since the terminal ends of the floss are not used and are discarded. In addition, many people have a great deal of difficulty administering dental floss held with fingers. Also, fingers must be inserted into the mouth which can be unsanitary, cumbersome, uncomfortable and distasteful. The user's fingers become coated with saliva and it is difficult to maintain a solid grip on the floss. When flossing with fingers, food particles and saliva are often ejected from the mouth only to land on a nearby surface such as a bathroom mirror.

Consequently, many different dental floss holders have been created to assist in the manipulation of dental floss. For example, U.S. Pat. Nos. 4,982,752 (Rodriguez), 3,642,011 (Thompson), 4,753,254 (McCollough et al.) and 2,811,162 (Brody) all disclose elongated flexible arm members that may be squeezed toward one another to fasten and hold in tension a length of floss. Upon their release, the arms apply tension to the floss. Other devices, such as U.S. Pat. Nos. 1,916,653 (Bodde), 5,105,840 (Giacopuzzi), 2,187,442 (Beach), 1,110,680 (Gamble), 5,123,432 (Wyss) and 5,197,498 (Stewart) apply tension to floss held between opposed pivoting members using scissor-type, tweezers-type, pliers or hand-grip type arrangements. While each of the patents described above is suitable for its intended purposes, for reasons discussed below, they suffer from one or more drawbacks.

Because teeth are often difficult to access, proper flossing is not an easy accomplishment. Often floss must be positioned between adjacent teeth that are contacting one another. Gaining access to the gum area below contacting teeth requires passing the floss through the contact region. As the floss passes through this contact region, it encounters considerable resistance and must be drawn tightly by the user to enable the application of an additional amount of force necessary for passage of the floss through the contact region.

Many of the dental floss holders described above, e.g., those having flexible arms arranged to be squeezed before fastening floss therebetween, appear not to be arranged to enable the application of any additional tension during use as may be required to enable access of floss to gum surfaces located below contacting teeth. Other dental floss holders described above, e.g., those where floss is held between opposed pivoting members using scissor-type, tweezers-type, pliers or hand-grip type arrangements, appear to rely upon manual actuation for application of additional tension.

The dental floss holder of this invention is arranged to enable the application of additional tension to floss during use in a manner that is not shown nor suggested in the prior art. In particular, the dental floss holder of the present invention is provided with an actuating device that is designed to be bitten upon by the user. In response to a user biting down on the actuating device, the dental floss holder will impart the additional tension required to enable passage of the floss between the contact region of two adjacent teeth.

OBJECTS OF THE INVENTION

An object of the present invention is to provide a dental floss holder that overcomes the disadvantages of the prior art.

Another object of the present invention is to provide a dental floss holder that provides a floss tensioning means to enable the abrasion and removal of plaque and food particles from interproximal surfaces of teeth.

Another object of the present invention is to provide a dental floss holder which is of convenient size to be held in the hand of the user while applying dental floss to the teeth.

Another object of the present invention is to provide a dental floss holder which is simple and durable in construction.

Another object of the present invention is to provide a dental floss holder which is inexpensive to manufacture.

Another object of the present invention is to provide a dental floss holder which is efficient and sanitary in use.

Another object of the present invention is to provide a dental floss holder which is neat and attractive in appearance.

Another object of the present invention is to provide a dental floss holder which is reliable in operation.

Another object of the present invention is to provide a dental floss holder that does not rely upon manual actuation to apply any additional amounts of tension on floss held therein.

Another object of the present invention is to provide a dental floss holder which reduces time of flossing.

Another object of the present invention is to provide a dental floss holder which facilitates the threading of dental floss prior to use.

Another object of the present invention is to provide a dental floss holder which is simple to use.

SUMMARY OF THE INVENTION

A dental flossing holder adapted to be held by a hand of a user for holding and manipulating a length of dental floss. The holder comprises a housing having an opening for dispensing a desired length of dental floss and a storage compartment located within the housing for storing dental floss to be dispensed. A tensioning means extends from the housing and comprises a pair of opposed support members each member having a free end. An anchoring means is located at the free end of each support member. The anchoring means is provided for removably anchoring the length of dental floss between the free ends of the support members. The support members are moveable with respect to each other from a first position defined by a first distance between the free ends to a second position defined by a second distance between the free ends, the second distance being greater than the first distance. An actuating means is coupled to the tensioning means and is operable in response to the user biting thereon to cause the support members to move from the first position to the second position to exert tension on the floss and enable the abrasion and removal of plaque and food particles from interproximal surfaces of teeth.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENT

Figure 1:
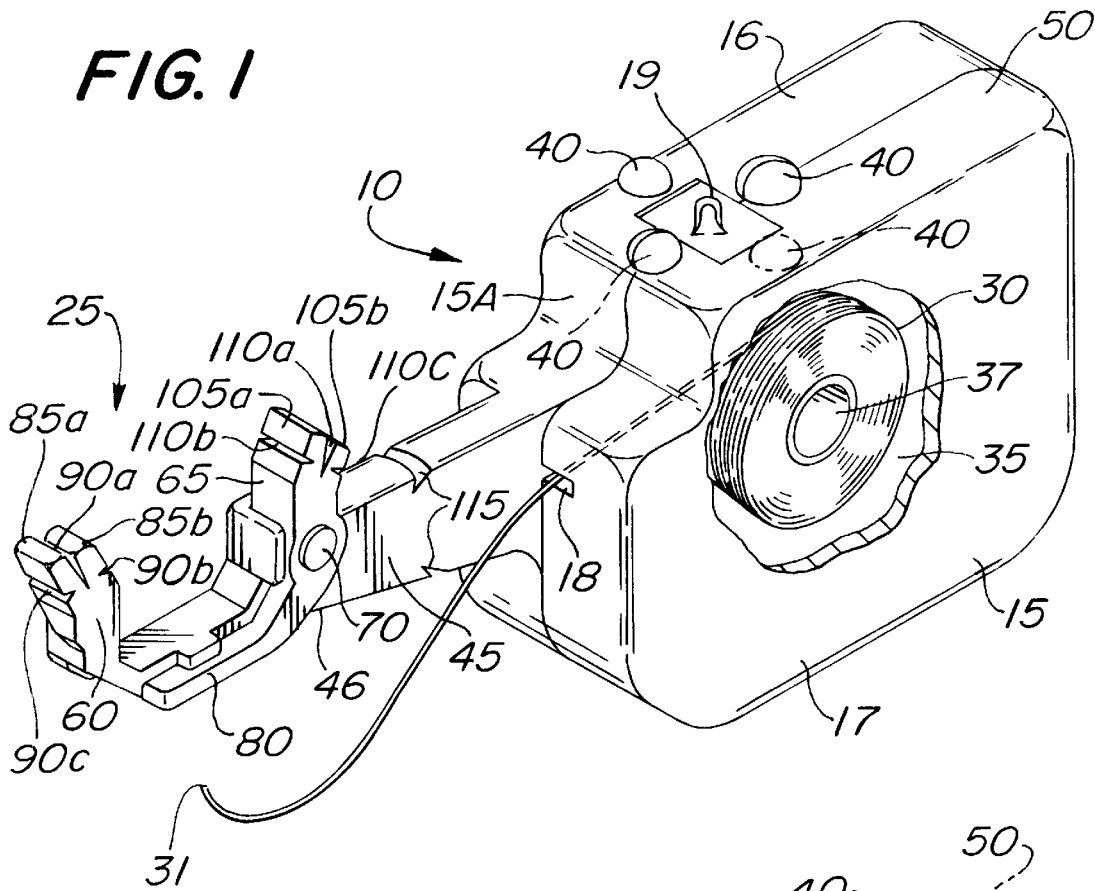
FIG. 1 is an enlarged isometric view of a first embodiment of the present invention, partially in section to reveal the storage compartment where a spool of dental floss is stored.
Figure 2:
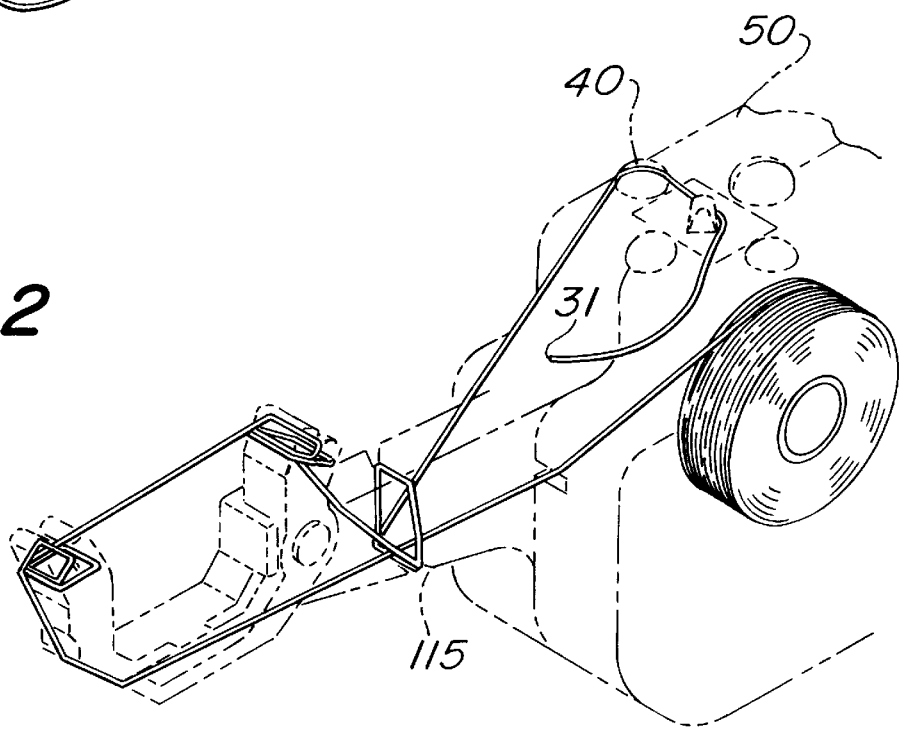
FIG. 2 is an enlarged isometric view of the first embodiment of the present invention illustrating a length of floss routed over the dental floss holder and anchored between the free ends of each support member for use.
Figure 3:
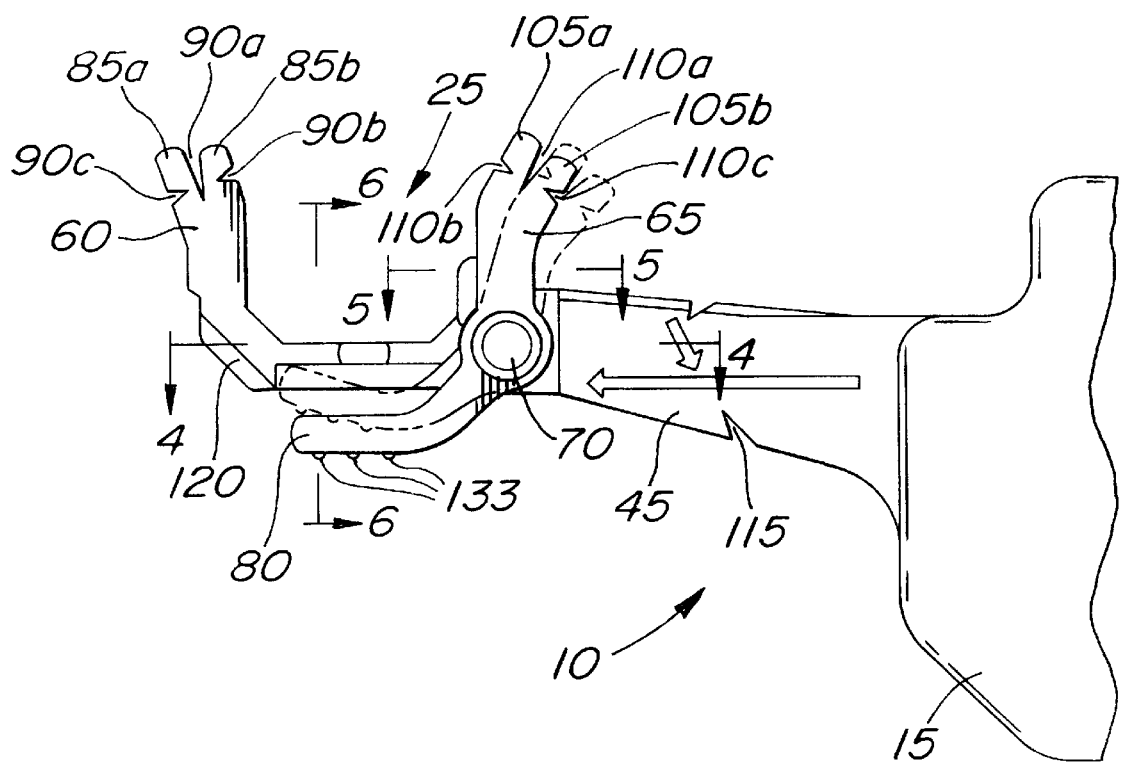
FIG. 3 is a enlarged partial side elevation view of the first embodiment of the device of the present invention illustrating the movement of the pivotable support member.

Referring now to various figures of the drawings where like reference numerals refer to like parts, there is shown at 10 in FIGS. 1 through 3, a dental floss holder with automatic floss tension means constructed in accordance with this invention. The details of the dental floss holder 10 will be described later. Suffice it for now to say that the embodiment 10 of the dental floss holder comprises a housing 15, a storage compartment 35 and a tensioning device 25 extending from the housing 15 for holding in tension a length of dental floss. Coupled to the tensioning device is an actuating means that is arranged to apply an additional tensile force upon the length of held dental floss when a user bites upon the actuating means. The increased tension enables the floss to pass through closely spaced or contacting teeth to enable removal of plaque and food particles from interproximal surfaces of the user's teeth and gum.

The housing 15 is designed and adapted to be easily grasped, held, and manipulated by one hand of the user and because of its shape enables portability of the dental floss holder 10. As best seen in FIG. 1, the housing 15 may have a generally box-shaped configuration having a cut-out notch 15a. The cut-out notch 15a is provided to enable ease in digital manipulation. Further, the housing 15 may also may also be provided with an irregular outer surface which is slightly roughened or textured, e.g., with ridges, to enable non-slip engagement. It should be understood, however, that the housing 15 may take any configuration which accomplishes the desired objectives. The dental floss holder can be formed of any suitable material and preferably molded plastic parts.

As best shown in FIG. 1, the housing is formed of a base portion 16 and a removable lid portion 17. Removal of the lid portion 17 from the base portion 16 permits access to an interior storage compartment 35. The lid portion 17 could be a piece that is separate from the base portion 16 or, alternatively, could be attached to the base portion 16 by any suitable hinge means, e.g., a living hinge (not shown). The storage compartment 35 serves to house a spool or bobbin of dental floss 30 in a compact manner. In particular, the storage compartment 35 is provided with a centrally located cylindrical spindle 37 which extends between the inner walls of the base portion 16 and the removable lid portion 17 of the housing 15. When the lid portion 17 of the housing 15 is removed from the base portion 16, the cylindrical spindle 37 is arranged to receive for rotatable mounting the spool or bobbin of dental floss 30 for dispensing of dental floss.

As best shown in FIGS. 1 and 2, the housing 15 is provided with an opening 18 which may be located in the lid portion 17 which allows one end 31 of the supply reel of dental floss 30 to extend outwardly from the storage compartment 35. The housing 15 is also provided with a raised metal tab 19 affixed between the base 16 and lid 17 portions. This tab 19, a well-known feature of dental floss containers, is provided with a cutting edge for cutting the floss. The tab 19 may be glued or otherwise affixed to the top surface of the housing 15.

Also best shown in FIGS. 1 and 2, the housing 15 is provided with a plurality of raised nodules 40 that surround the raised metal tab 19. Each raised nodule 40 is provided for enabling the user to route dental floss therearound prior to cutting the dental floss using the raised metal tab 19. In this manner, each raised nodule 40 acts to protect the user's fingers from being cut on the exposed cutting edge of the raised metal tab 19 during cutting of floss. It should be understood that fewer nodules 40 than are shown in FIG. 1, e.g., one to three, could be situated around the raised metal tab 19 to accomplish the same purpose, i.e., protecting the user's fingers from cutting during cutting of dental floss.

Figure 8:
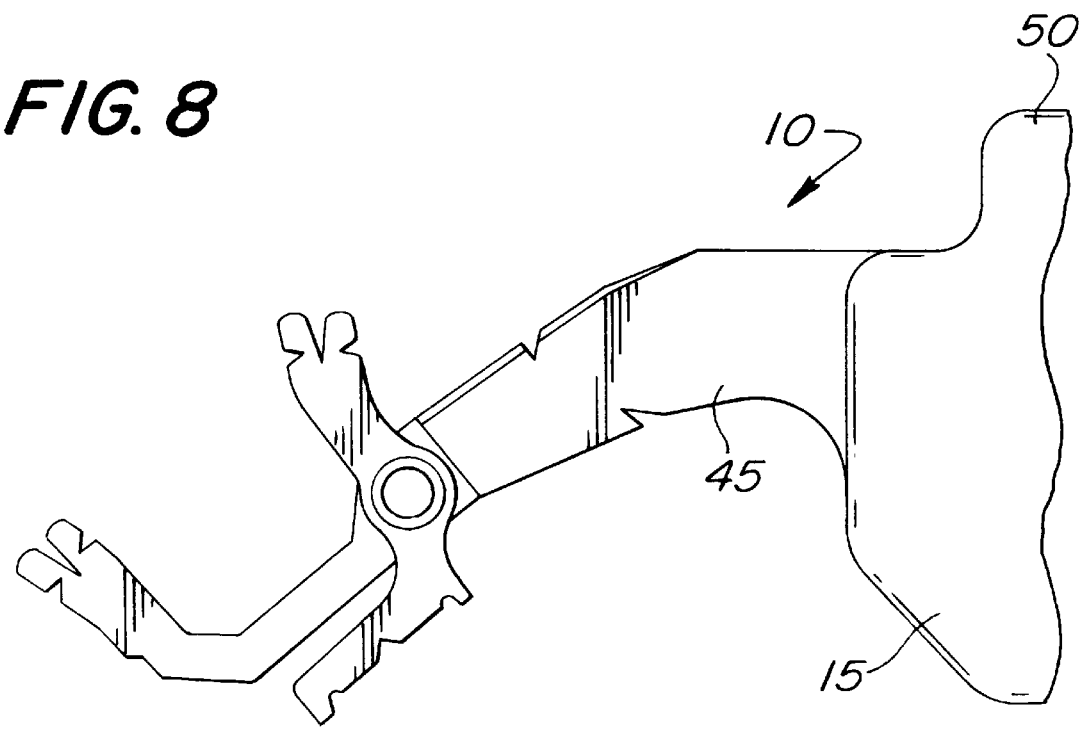
FIG. 8 is an enlarged partial side elevational view of a third embodiment of the device of the present invention.

Referring again to FIGS. 1 through 3, the tensioning device 25 is connected to the housing 15 by means of an extension arm 45 that is integral with the housing and extends laterally therefrom. As shown in FIGS. 1 and 2, the extension arm 45 extends from the housing 15 along a path that is roughly parallel to the top surface 50 of the housing 15. However, as best shown in FIG. 8, the extension arm 45 could extend at a downward angle with respect to the top surface of the housing 15. Orienting the extension arm 45 to descend downwardly at an angle, e.g., twenty to thirty degrees, with respect to the top surface 50 of the housing 15 as the arm extends away from the housing will serve to minimize the potential interference of the housing while the user is attaching or wrapping dental floss to the tensioning device in the manner to be described in detail below. It should be understood that this aspect of the invention could be applied to any of the embodiments described heretofore or hereinafter.

Preferably, the extension arm 45 is provided with an irregular outer surface which is slightly roughened or textured to enable nonslip engagement of the user's fingers during use of the dental floss holder 10. Any irregular surface could be used, including ridges running laterally along an underside portion of the arm 46 to enable nonslip engagement of the user's thumb during use.

Figure 4:
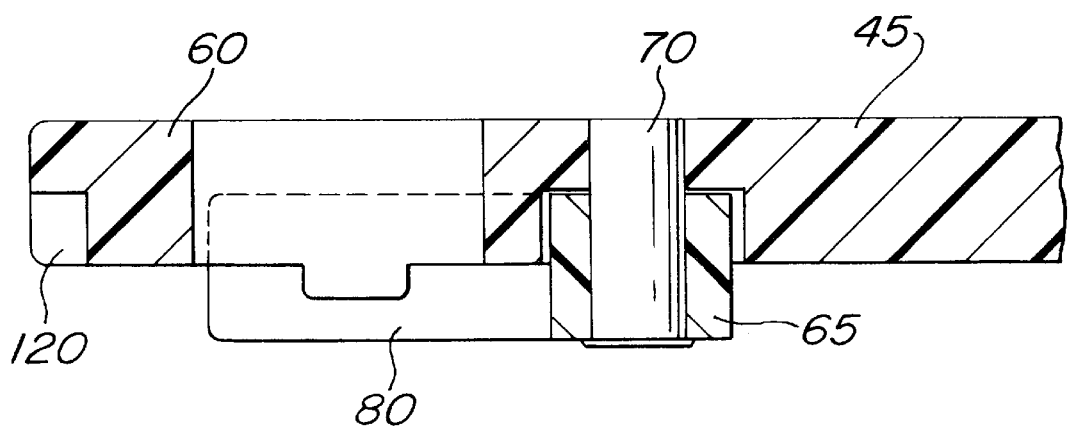
FIG. 4 is an enlarged sectional view taken along line 4—4 of FIG. 3.
Figure 5:
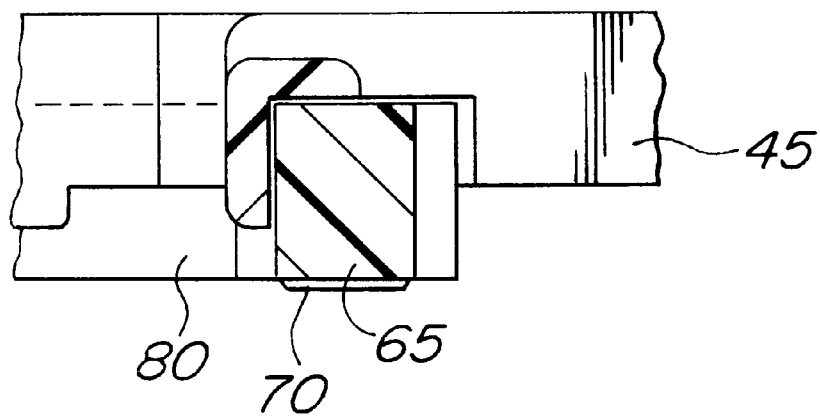
FIG. 5 is an enlarged sectional view taken along line 5—5 of FIG. 3.
Figure 6:
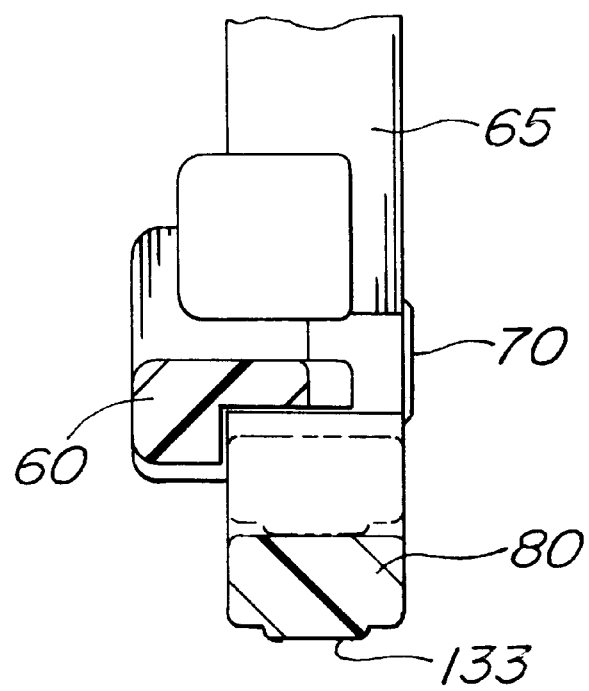
FIG. 6 is an enlarged sectional view taken along line 6—6 of FIG. 3.

As shown in FIGS. 1 and 2, the tensioning device 25 is disposed at the end of the extension arm 45 opposite the housing 15 and comprises a stationary support member 60 and a pivotable support member 65. The pivotable support member 65 is hingedly secured to the stationary support member 60 by any suitable hinging means. As best shown in FIG. 4, the pivotable support member 65 is hingedly secured to the stationary support member 60 by means of a bolt 70 which extends through openings in both support members 60 and 65. The hinged attachment of the pivotable support member 65 to the stationary support member 60 by means of the bolt or screw 70 is best illustrated in FIG. 4. In a more preferable alternative embodiment (not shown), rather than utilizing a distinct bolt 70 to enable hinged attachment of the support members, the stationary support member 60 could be provided with a post integral with the stationary support member and formed of any suitable material, e.g., plastic, to enable hinged attachment of the pivotable support member 65 thereto. An actuating member 80, integral with the pivotable support member 65 extends downwardly and laterally from the bolt 70.

Referring now to FIGS. 1 through 3, the stationary support member 60 includes an upwardly extending curved arm that terminates at an extremity having a plurality of grooves 90a, 90b and 90c which are adapted for receiving and anchoring a length of dental floss 30 for use in cleaning and removing debris from the teeth. Likewise, the pivotable support member 65 includes an upwardly extending curved arm that ends at an extremity having a plurality of grooves 110a, 110b and 110c. The curved arms are opposed and spaced a sufficient distance from one another to enable the user to reciprocate the dental floss holder in an up-and-down or side-to-side fashion in relation to front or molar teeth for cleansing and removal of debris from the teeth and gums.

As best shown in FIG. 3, the groove 90a extends from the extremity of the stationary support member 60 through a pair of opposed pinch grooves 90b and 90c to a point located therebelow which divides the extremity into two portions, 85a and 85b. In this manner, dental floss threaded through groove 90a can be secured therein by thereafter tightly wrapping the dental floss around the opposed pinch grooves 90b and 90c thus causing extremity portions 85a and 85b to come together and pinch the dental floss disposed within groove 90a. Dental floss threaded through groove 110a is pinched therein in a similar manner.

The routing of the floss is best illustrated by reference to FIGS. 1 and 2. When practicing the invention, the user first pulls a length of floss through the opening 18. This floss is then positioned against or along an abutment track 120 (FIG. 3) located at the lower portion of stationary support member 60. The length of floss is then routed through groove 90a and tightly wrapped around pinch grooves 90b and 90c thus causing extremity portions 85a and 85b to squeeze together and pinch the floss within groove 90a. The length of floss is then stretched in tension across a span located between the extremities of the support members 60 and 65 and then routed through the groove 110a. Thereafter, the floss is tightly wrapped around pinch grooves 110b and 110c thus causing extremity portions 105a and 105b to squeeze together and pinch the dental floss within the groove 110a. In this manner, the length of floss stretched across the span is held in tension between the extremities and without slippage during use of the dental floss holder of this invention. The remaining length of floss is then secured within an anchoring notches 115 located in the extension arm 45. The remaining length of floss is then routed around one of the nodules 40 located on the top of the housing and is cut on the cutting edge of the raised metal tab 19.

Also, as best shown in FIG. 2, each of grooves 90a, 90b, 90c, 110a, 110b and 110c is formed of a length that follows a direction that is perpendicular to the length of dental floss spanning between the extremities of the support members 60 and 65. Orienting grooves in this manner provides manufacturing advantages including the simplification of the plastic molding process.

Referring again to FIGS. 1–3, during typical operation of the dental floss holder, the loaded span of dental floss 30 is positioned between two adjacent teeth. In many cases, adjacent teeth will be in contact with one another thus requiring the user to draw the floss tightly to enable the application of an additional amount of force necessary for passage of the floss through the contact region.

In this manner, the dental floss holder of the present invention is provided with an actuating member 80 which is shown as being integral with the pivotable support member 65. Under this embodiment, the actuating member 80 extends downwardly from the pivot point defined at 70 and extends laterally under a portion of the stationary support member 60. Referring again to FIG. 3, the actuating member 80 is provided with a bottom surface having a plurality of bite contacting nodules 133 which are arranged to engage a user's teeth when he or she bites thereon. In response to the user biting and engaging the bite contacting nodules 133, the actuating member 80 rotates in a clockwise direction from a first position (shown in solid lines) through to a second position (shown in phantom lines) whereupon the actuating member 80 eventually comes into abutting relation with the bottom surface of the stationary member 60. Likewise, the extremity of the pivotable support member 65 moves clockwise from a first position (shown in solid lines), located closer to the extremity of the stationary member 60, to a second position (shown in phantom lines) that is a distance further away from the extremity of the stationary member. Movement of the pivotable extremity in this manner causes the dental floss located within the spanned distance between the extremities to come under additional tension. This additional tension enables the user to exert the additional force that may be necessary for the floss to pass through contacting teeth to enable the abrasion and removal of plaque and food particles from interproximal surfaces of the user's teeth and gum.

Figure 7:
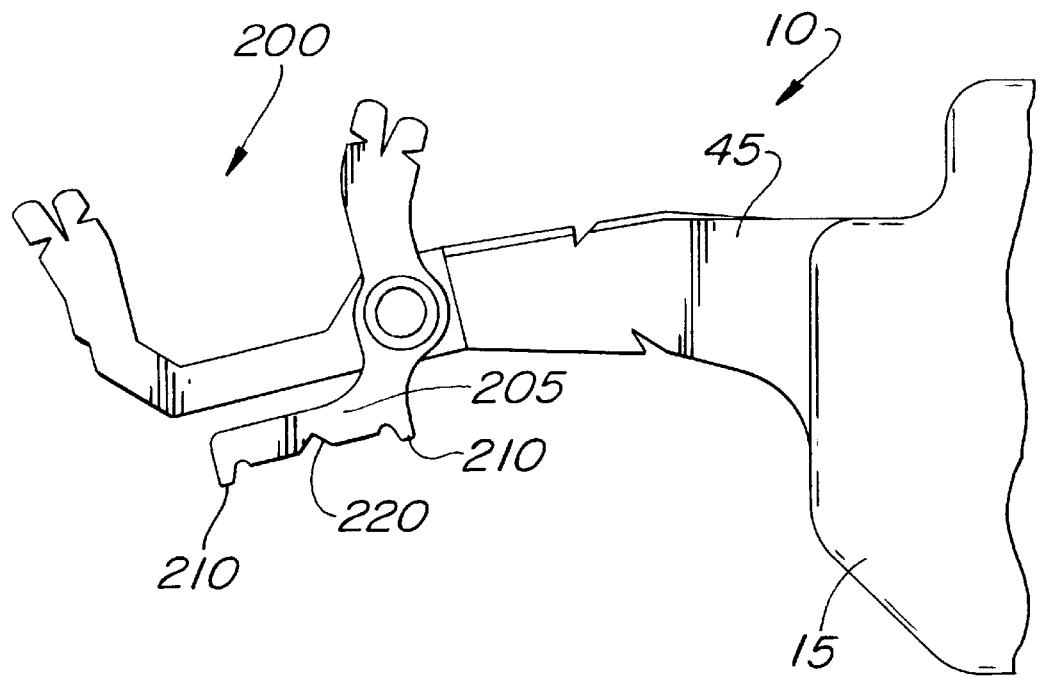
FIG. 7 is an enlarged partial side elevational view of a second embodiment of the device of the present invention.

Referring now to FIG. 7, there is shown at 200 an alternative embodiment of the present invention. Rather than being provided with bite contacting nodules as described in the first embodiment, the actuatable member 205 of this embodiment is provided with a feature on its bottom surface to enable engagement with either the user's front teeth or back molar teeth. In particular, the underside surface is provided with a pair of downwardly extending molar containment flanges 210 that act to contain a back molar during biting. In this manner, during flossing of adjacent contacting upper molars, the user may activate the actuating member 205 by biting thereon with a lower molar which will be contained within the molar containment flanges 210. In turn, the dental floss holder 200 will provide increased tension to the floss to enable its passage through contacting upper molars. Similarly, during flossing of contacting lower molars, the user may activate the actuating member by biting thereon with an upper molar which will be contained within the molar containment flanges 210. In turn, the dental floss holder 200 will provide increased tension necessary to enable passage of floss through contacting lower molars.

The actuatable member 205 shown in FIG. 7 is also provided with a groove 220 that enables the user to engage the actuating member with a front tooth. In this manner, during flossing of contacting upper front teeth, the user may activate the actuating member 205 by biting thereon with lower front teeth which will be contained within the groove 220. In turn, the dental floss holder 200 will provide additional tension on the floss necessary to enable passage of the dental floss through contacting front upper front teeth.

As best shown in FIG. 8, the embodiment shown therein, which features the extension arm 45 extending downwardly with respect to the top surface of the housing 15, may also include an actuating member having molar containment flanges and a groove. Moreover, the actuating member having molar containment flanges and a groove, as previously described, could be incorporated into any of the other embodiments described heretofore or hereinafter.

Figure 9:
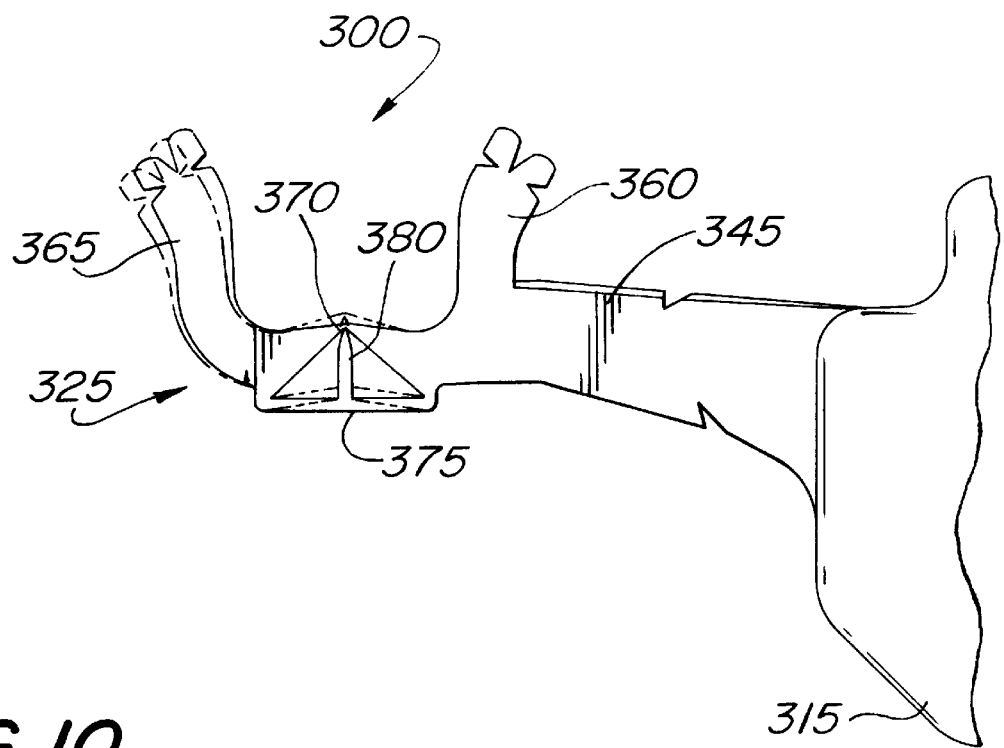
FIG. 9 is an enlarged partial side elevational view of a fourth embodiment of the device of the present invention.

Referring now to FIG. 9, there is shown at 300 a second alternative embodiment of the present invention. As in the embodiments described above, this embodiment includes a housing 315 having an internal storage compartment (not shown) for storing a spool or bobbin of dental floss in a compact manner. The housing 315 of this embodiment could also be provided with many of the same features as described above in connection with the earlier described embodiments, e.g., raised nodules, raised metal tab, actuating means including molar containment flanges and a groove for engaging front teeth, etc. As in earlier embodiments, this embodiment also includes an extension arm 345 integral with the housing which extends laterally from the housing 315. Attached at the end of the extension arm 345 opposite the housing 315 is a tensioning device 325. As shown in FIG. 9, the extension arm 345 extends from the housing 315 along a path that is roughly parallel to the top surface (not shown) of the housing 315. However, the extension arm 345 of this embodiment could extend at a downward angle with respect to the top surface of the housing 315 as shown in the embodiment of FIG. 8. As previously explained in connection with the first embodiment, orienting the arm in this manner with respect to the housing will serve to minimize the potential interference of the housing while the user is attaching dental floss. The tensioning device 325 comprises upwardly extending curved arms that form a stationary support member 360 and a pivotable support member 365. Each support member is provided with grooves at its extremity to enable the threading therethrough and pinching of dental floss in a manner similar to that previously described and shown in FIG. 2.

The pivotable support member 365 is connected to the stationary support member 360 through a hinge 370 and a horizontally disposed actuatable member 375 formed of a thin, flexible material. A vertical member 380 is disposed between the hinge 370 and the actuatable member 375. As shown in phantom in FIG. 9, during operation, the thin flexible actuatable member 375 is arranged to engage a user's teeth and flex in response to the user biting thereon. In flexing, the actuating member 375 deflects upwardly thus causing the vertical member 380 to be driven upwardly which in turn causes the pivotable support member 365 to rotate counterclockwise about the hinge 370. The extremity of the pivotable support member moves from a first distance (shown in solid line) to a second distance further away from the extremity of the stationary support member (shown in phantom line). Movement of the extremity of the pivotable support member 365 in this manner causes the dental floss located within the spanned distance between the extremities of the support members 360, 365 to come under additional tension. This additional tension enables the user to exert additional force necessary to pass floss through the contacting teeth as discussed previously. Although not shown in FIG. 9, the actuating member 375 may be provided with bite contacting nodules similar to those previously discussed and illustrated in FIG. 3 for engaging teeth or with molar containment flanges and a groove for containing front teeth as previously described and illustrated in FIGS. 7 and 8.

Figure 10:
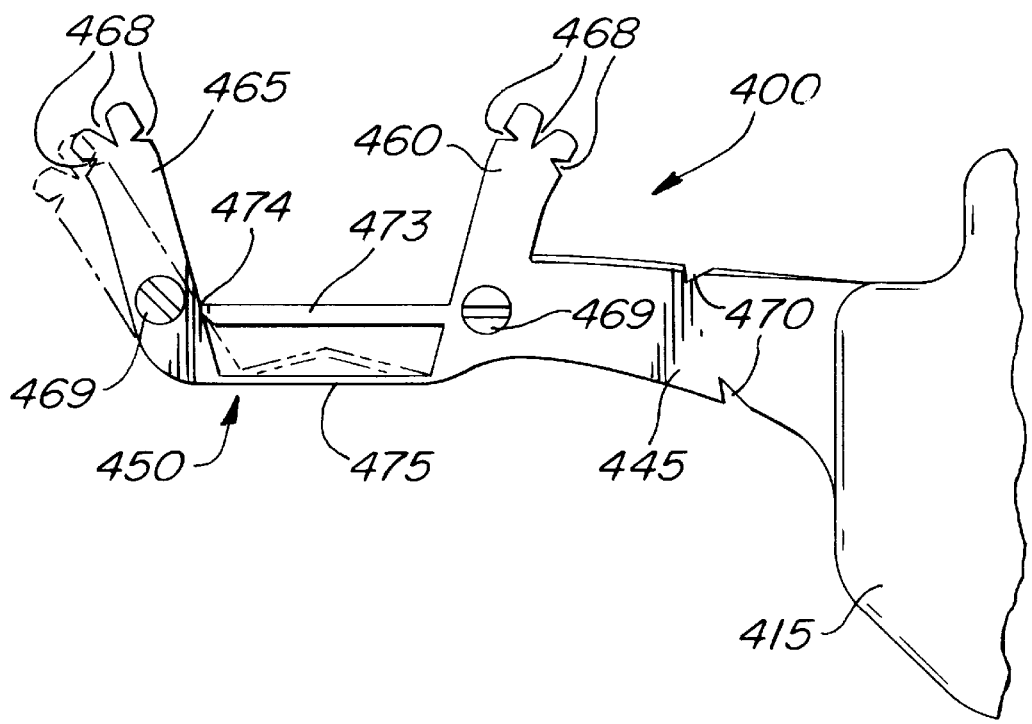
FIG. 10 is an enlarged partial side elevational view of the preferred embodiment of the device of the present invention.

Referring now to FIG. 10, there is shown at 400 the preferred embodiment of the present invention. As in the embodiments described previously, this embodiment 400 also includes a housing 415 having an internal storage compartment (not shown) for storing a spool or bobbin of dental floss in a compact manner. The housing 415 of this embodiment may also be provided with some or all of the same features as shown and described in the embodiments set forth above, e.g., a roughened outer surface to enable ease of digital manipulation, raised nodules for routing dental floss before cutting, a raised metal tab for cutting dental floss, etc. As in earlier embodiments, this embodiment also includes an extension arm 445 which may be integral with the housing and extends laterally from the housing 415. The extension arm 445 is also provided with a plurality of anchoring grooves 470 for securing a remaining length of floss after the floss has been secured to the extremities of the support member.

Attached at the end of the extension arm 445 opposite the housing 415 is a tensioning device 450 comprising upwardly extending arms that form a stationary support member 460 and a pivotable support member 465 each having a plurality of grooves 468 located at their extremities to enable the threading of dental floss therethrough in a manner similar to that previously described and shown in FIG. 2. A plurality of slotted nodules 469 are disposed on the tensioning device 450 for routing and anchoring of dental floss.

The extension arm 445 is shown in FIG. 10 as extending from the housing 415 along a path that is roughly parallel to the top surface (not shown) of the housing 415. However, the extension arm 445 of this embodiment could extend at a downward angle with respect to the top surface of the housing 415 such as shown in the embodiment of FIG. 8. As previously explained in connection with the embodiment shown in FIG. 8, orienting the extension arm 445 in this manner with respect to the housing 415 will serve to minimize the potential interference of the housing while the user is routing and attaching dental floss to the grooves 468 located at the extremities of the stationary and pivotable support members 460, 465. The remaining length of floss is then secured within the anchoring grooves 470 located on the extension arm 445.

The pivotable support member 465 is connected to the stationary support member 460 through a horizontally disposed thickened web 473 and a horizontally disposed deflectable member 475 formed of a thin, flexible material. As shown in FIG. 10, during operation, the deflectable member 475 is arranged to engage a user's teeth and the center portion of the member 475 is arranged to deflect upwardly (shown in phantom lines) in response to the user biting thereon. This upward deflection causes the pivotable support member 465 to rotate counterclockwise at a pivot point 474. The extremity of the pivotable support member 465 moves from a first position (shown in solid line) wherein the extremity is a first distance from the extremity of the stationary member 460 to a second position (shown in phantom lines) where the extremity is a further distance from the extremity of the stationary member 460. Movement of the extremity of the pivotable support member 465 in this manner causes the dental floss located within the spanned distance between the extremities of the support members 460, 465 to come under additional tension. This additional tension enables the user to exert additional force necessary to pass floss through the contacting or closely spaced teeth as discussed previously.

Although not shown in FIG. 10, the bottom surface of the actuating member 475 may be provided with bite contacting nodules similar to those previously discussed and illustrated in FIG. 3 for engaging teeth or with molar containment flanges and a groove for containing front teeth as previously described and illustrated in FIGS. 7 and 8.

This invention is not limited to the precise embodiments described above with reference to the drawings, and various modifications are feasible within the scope of the ensuing claims.

I claim:

1. A dental floss holder adapted to be held by a hand of a user for holding and manipulating a length of dental floss, said holder comprising:
   a. tensioning means comprising opposed support members;
   b. anchoring means located on each said support member, said anchoring means being provided for removably anchoring the length of dental floss extending between said support members;
   c. said support members being moveable with respect to each other from a first position defined by a first distance between said anchoring means to a second position defined by a second distance between said anchoring means, said second distance being greater than said first distance; and,
   d. actuating means coupled to said tensioning means, said actuating means being operable in response to the user biting thereon to cause said support members to move from said first position to said second position to exert tension on the length of floss extending between said support members.

2. The dental floss holder of claim 1 wherein each said support member further comprises a free end, said anchoring means being located at said free end of each said support member.

3. The dental floss holder of claim 1 wherein each said anchoring means comprises a plurality of grooves.

4. The dental floss holder of claim 3 wherein said plurality of grooves includes opposed pinch grooves that are spaced apart.

5. The dental floss holder of claim 4 additionally comprising a third groove extending between said opposed pinch grooves that are spaced apart to provide an ability to pinch dental floss threaded through said third groove.

6. The dental floss holder of claim 5 wherein the length of dental floss extending between said support members lies in a first direction and wherein said opposed pinch grooves and said third groove each lie in a direction that is perpendicular to said first direction.

7. The dental floss holder of claim 4 wherein said opposed support members comprise a first support member and a second support member, said second support member being hingedly connected to said first support member at a pivot point and being moveable with respect to said first support member.

8. The dental floss holder of claim 7 wherein said actuating means is integral with said second support member, said actuating means extending downwardly and laterally from said pivot point and having a free end.

9. The dental floss holder of claim 7 wherein said first support member additionally comprises an extension arm extending laterally therefrom, said extension arm comprising at least one anchoring notch disposed thereon for routing and anchoring dental floss.

10. The dental floss holder of claim 1 wherein said opposed support members comprise a first support member and a second support member, said second support member being hingedly connected to said first support member at a pivot point and being moveable with respect to said first support member, said actuating means comprising a thin deflectable web connected to and extending between said first support member and said second support member, said deflectable web being arranged to deflect in response to a user biting thereon.

11. The dental floss holder of claim 10 additionally comprising a vertical member disposed on said deflectable web and extending upwardly therefrom towards said pivot point.

12. The dental floss holder of claim 1 wherein said opposed support members comprise a first support member and a second support member, said second support member being hingedly connected to said first support member at a pivot point and being moveable with respect to said first support member, said actuating means comprises a thin deflectable web connected to and extending between said first support member and said second support member, said deflectable web being arranged to deflect in response to a user biting thereon, said holder additionally comprising a second web also connected to and extending between said first support member and said second support member, said second web being located above said deflectable web.

13. The dental floss holder of claim 1 wherein said actuating means additionally comprises a bottom surface having a plurality of bite contacting nodules disposed thereon, said bite contacting nodules being arranged to engage a user's teeth during biting.

14. The dental floss holder of claim 1 wherein said actuating means additionally comprises a bottom surface having molar containment means disposed thereon.

15. The dental floss holder of claim 14 wherein said molar containment means comprises spaced-apart opposed downwardly extending flange members.

16. The dental floss holder of claim 15 wherein said bottom surface additionally comprises a front tooth containment means comprising a groove.

17. The dental floss holder of claim 1 wherein said actuating means additionally comprises a bottom surface having a front tooth containment means.

18. The dental floss holder of claim 17 wherein said front tooth containment means comprises a groove.

* * * * *